United States Patent [19]

Pachys

[11] Patent Number: 5,603,728
[45] Date of Patent: Feb. 18, 1997

[54] SCALP COOLING/HEATING APPARATUS

[76] Inventor: Freddy Pachys, P.O. Box 18368, Jerusalem 91181, Israel

[21] Appl. No.: 262,284

[22] Filed: Jun. 20, 1994

[51] Int. Cl.$^6$ .................................................. A61F 7/00
[52] U.S. Cl. ............................ 607/110; 607/98; 607/104
[58] Field of Search ................................ 128/96, 98, 104, 128/108–112, 114

[56] References Cited

U.S. PATENT DOCUMENTS

| | | | |
|---|---|---|---|
| 1,710,882 | 4/1929 | Larson | 607/110 X |
| 4,061,898 | 12/1977 | Murray et al. | 607/110 X |
| 4,459,471 | 7/1984 | Hulett et al. | 607/110 X |
| 5,292,347 | 3/1994 | Pompei | 607/110 X |
| 5,304,213 | 4/1994 | Berke et al. | 607/114 X |
| 5,342,411 | 8/1994 | Maxted et al. | 607/110 X |
| 5,353,605 | 10/1994 | Naaman | 607/110 X |

*Primary Examiner*—Angela D. Sykes
*Attorney, Agent, or Firm*—Mark M. Friedman

[57] ABSTRACT

Scalp apparatus for regulating the temperature of the scalp of a wearer. The scalp apparatus includes a helmet for coveting the hair bearing scalp of the wearer, spacing means to provide an air space between the helmet and the scalp of the wearer and relating apparatus for regulating the temperature of the helmet so as to relate the temperature of the air space such that the scalp of the wearer is maintained at a desired temperature. The relating apparatus can be in the form of thermoelectric elements and a power supply for providing electrical power to the thermoelectric elements or a potion of piping and a source of fluid for providing a flow of liquid through the potion of piping. The apparatus can further include thermostate apparatus for controlling the regulating apparatus. The scalp apparatus can be employed for cooling the scalp of a wearer to combat the problem of alopecia during chemotherapy treatment or for warming the scalp of the wearer during heat treatments.

16 Claims, 5 Drawing Sheets

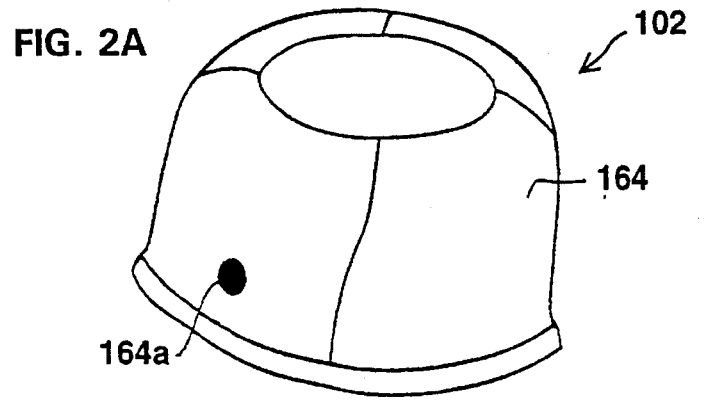
FIG. 2A
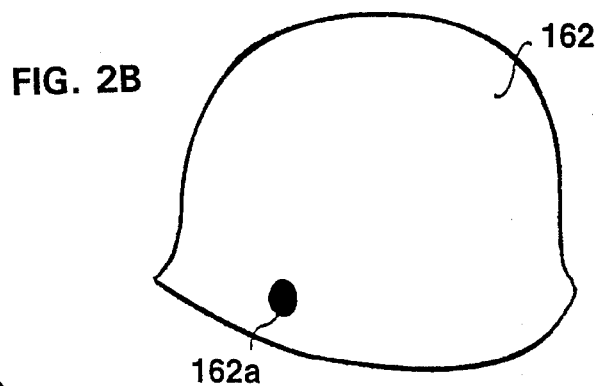
FIG. 2B
FIG. 2D
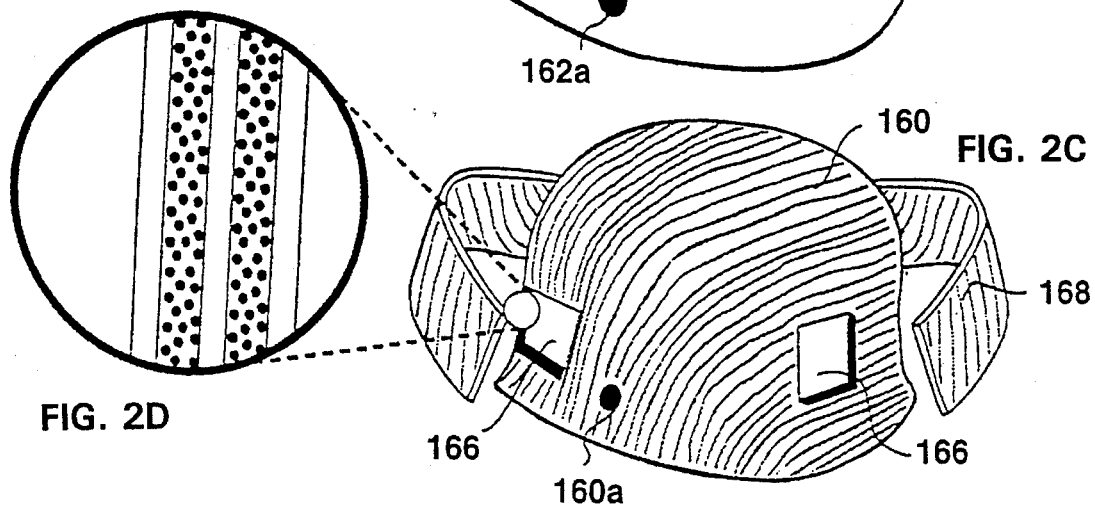
FIG. 2C
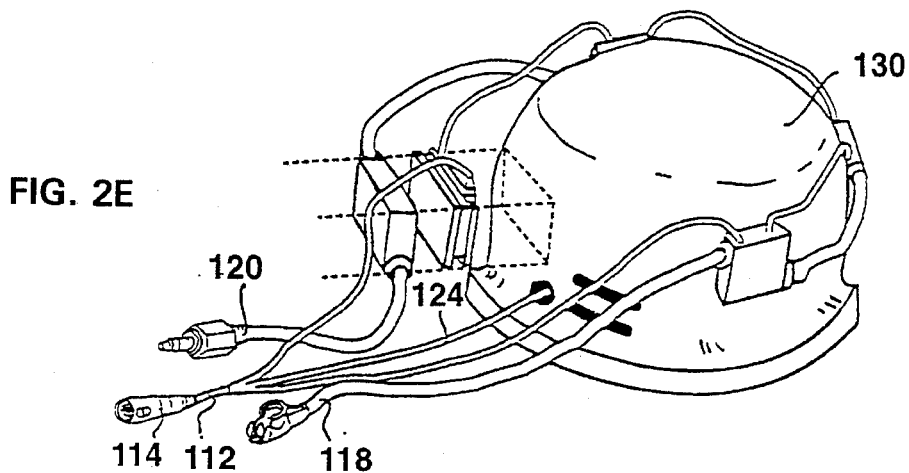
FIG. 2E 5,603,728

SCALP COOLING/HEATING APPARATUS

FIELD AND BACKGROUND OF THE INVENTION

The present invention relates to scalp apparatus for regulating the temperature of the scalp of a wearer in general and in particular to scalp apparatus in which the temperature of the scalp of the wearer is regulated by natural convection.

The use of cytotoxic agents in, for example, chemotherapy of cancer patients almost always leads to hair loss known as alopecia. Alopecia can be prevented by cooling the hair bearing scalp because drug uptake by hair follicles is reduced as a consequence of cutaneous vasoconstriction and the inhibition of cellular metabolic pathways. Other treatments are known for different medical conditions which require heating the scalp of the user.

Conventional apparatus for achieving regulation of the temperature of the scalp of a wearer entails direct cooling or heating of the scalp of the user. Conventional apparatus falls into three basic categories, which for sake of explanation, are described for cooling the scalp of a wearer. The first type of apparatus, as described in U.S. Pat. No. 4,522,149 to Tatsuki, includes the application of crushed ice compresses or shaped cryogen packs against the scalp of the wearer. In a similar application for facilitating post-traumatic, post-surgical and/or post-inflammatory healing of tissue, U.S. Pat. No. 5,169,384 to Bosniak et al., teaches the use of thermoelectric elements for cooling fluid filled deformable members which are in physical engagement with an underlying skin surface. The second type of apparatus, as described in U.S. Pat. No. 4,566,455 to Kramer, includes the circulation of chilled liquid in close thermal contact with the scalp. And the third type of apparatus, as described in WO 89/09583 to Maxted et al., includes the forced circulation of cold air in a closed air space surrounding the scalp of the wearer for cooling the scalp through the wind-chill effect.

These techniques suffer from a number of disadvantages. First, they often require pre-treatment in the form of hair-wetting for improving cooling. Second, condensation typically forms on the inside and/or outside of the head cooling implement which eventually forms dewdrops which run down onto the wearer's face. Third, the wearer often suffers uncomfortable sensations of either "cold-shock" by the application of cold assemblies against his scalp or "wind-chill" by the forced circulation of cold air. And finally, the head cooling implement often has to be provided in several sizes for fitting a wide range of wearers.

Therefore, it would be highly desirable to have a scalp apparatus for regulating the temperature of the scalp of a wearer without the aforementioned deficiencies.

SUMMARY OF THE INVENTION

The present invention is for a scalp apparatus for regulating the temperature of the scalp of a wearer. The scalp apparatus can be employed for either cooling or heating the scalp of the wearer depending on the required treatment.

Hence, according to the teachings of the present invention, there is provided scalp apparatus for regulating the temperature of the scalp of a wearer, the scalp apparatus comprising: (a) a helmet for covering at least a portion of the scalp of the wearer; (b) spacing means to provide an air space between the helmet and the scalp of the wearer; and (c) regulating for regulating the temperature of the helmet so as to regulate the temperature of the air space such that the temperature of the scalp of the wearer is maintained at a desired temperature.

According to further features of the present invention, the regulating means includes: (i) at least one thermoelectric element in thermal communication with the helmet, and (ii) a power supply for providing electrical power to said at least one thermoelectric element. The thermoelectric elements can be employed such that cooling surfaces are disposed toward the scalp of the wearer for cooling the scalp of the wearer or heating surfaces are disposed toward the scalp of the wearer for heating the scalp of the wearer. The thermoelectric elements can be electrically linked either in series or in parallel to the power supply.

According to still further features of the present invention, the scalp apparatus can include moderating means for moderating the temperature of the at least one thermoelectric element. The moderating means includes: (i) at least one thermal conductive element in thermal communication with the at least one thermoelectric element, and (ii) a source of fluid for moderating the temperature of the at least one thermal conductive element. The thermal conductive elements can be linked either in series or in parallel to the source of fluid.

According to yet still further features of the present invention, the regulating means includes: (i) a portion of piping in thermal communication with the helmet, and (ii) a source of fluid for providing a flow of liquid through the portion of piping.

According to yet still further features of the present invention, the scalp apparatus includes thermostat apparatus for controlling the regulating means wherein the thermostat apparatus includes a thermometer.

BRIEF DESCRIPTION OF THE DRAWINGS

The invention is herein described, by way of example only, with reference to the accompanying drawings, wherein:

FIG. 2 shows the multi-ply construction of the hat of the scalp apparatus;

DESCRIPTION OF THE PREFERRED EMBODIMENTS

Figure 1A:
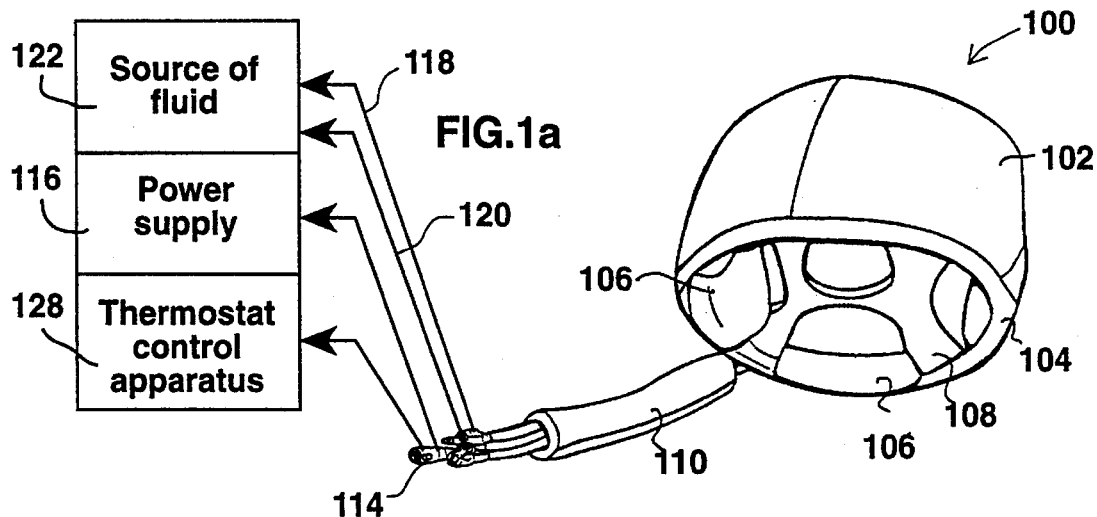
FIG. 1a shows a schematic view of scalp apparatus for regulating the temperature of the scalp of a wearer according to the teachings of the present invention.
Figure 1B:
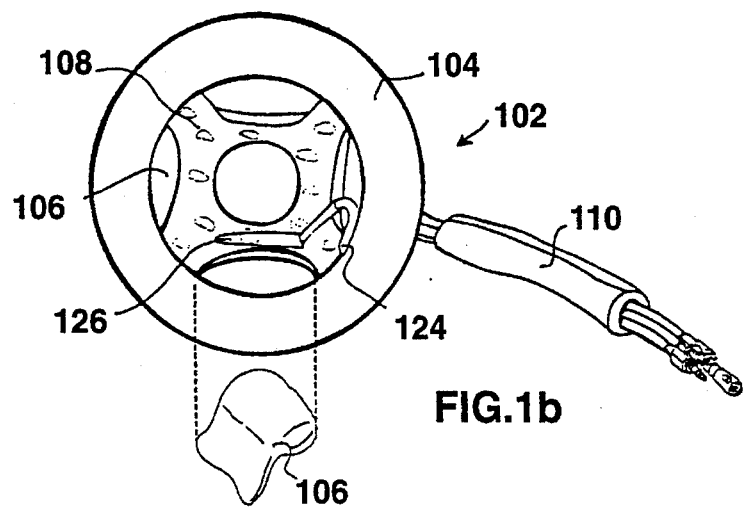
FIG. 1b shows a bottom view of the hat of the scalp apparatus.
Figure 1C:
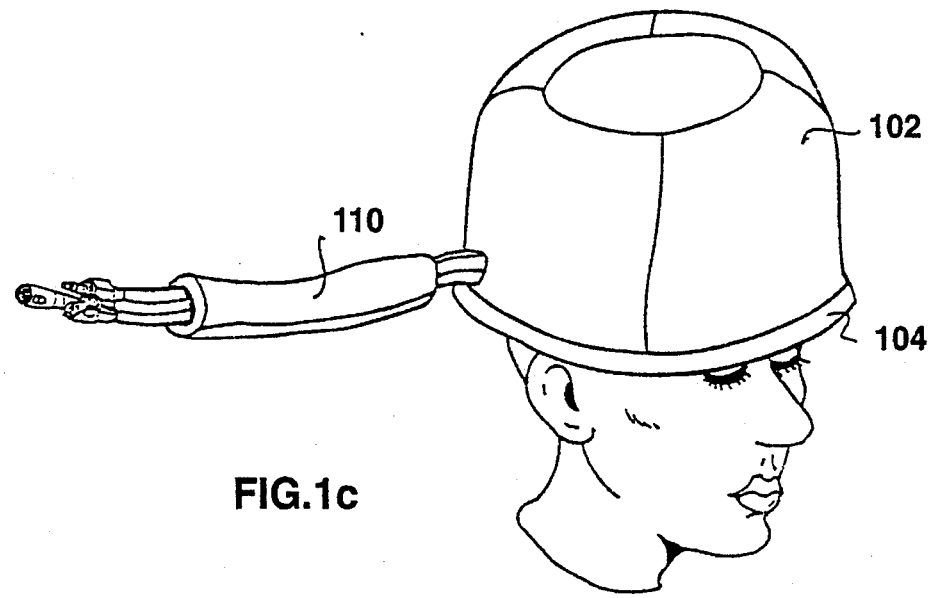
FIG. 1c shows a perspective view of the hat of the scalp apparatus donned by a wearer.
Figure 1D:
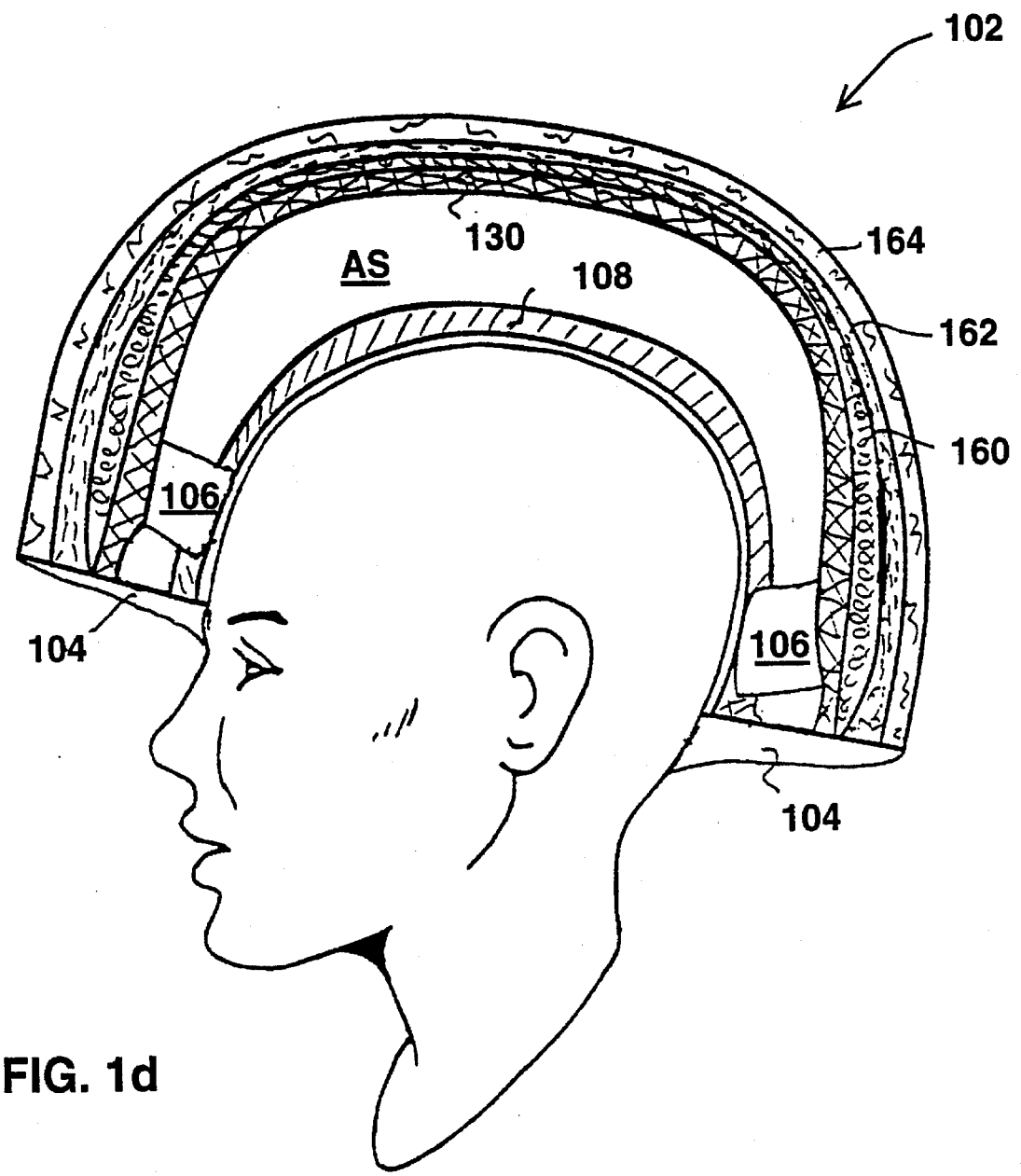
FIG. 1d shows a cross-sectional view of the hat donned by a wearer showing the air space between the helmet of the hat and the scalp of the wearer.

The present invention is of a scalp apparatus for regulating the temperature of the scalp of a wearer. The scalp apparatus can be employed for either cooling or heating the scalp of the wearer depending on the required treatment.

The principles and operation of the scalp apparatus of the present invention may be better understood with reference to the drawings and the accompanying description.

With reference now to the drawings, FIGS. 1a–1d show a preferred embodiment of a scalp apparatus, generally designated 100, constructed and operative according to the teachings of the present invention, for regulating the temperature of the scalp of a wearer.

Scalp apparatus 100 includes a tall crowned hat 102 having a headband 104 embracing the hairline of a wearer. Hat 102 includes one or more spacing elements for spacing hat 102 from the scalp of the wearer, thereby establishing an air space, denoted AS in FIG. 1d, therebetween. Spacing elements include a number of cushions 106 disposed around the periphery of headband 104 for spacing the rim of hat 102 from the scalp of the wearer and a headpiece 108 for spacing the crown of hat 102 from the scalp of the wearer. Headband 104 is preferably elasticated to ensure that the air space is substantially isolated from the surrounding environment. Preferably, hat 102 avoids inclusion of the ears of the wearer or headband 104 includes recesses which extend around the ears of the wearer.

Extending from hat 102 are a bundle 110 of wires and tubes for connecting elements, best seen in FIG. 2, deployed in hat 102 to external sources. Bundle 110 includes a lead 112 having a pin connector 114 for connection to an electric power supply 116 for providing electric power to thermoelectric elements used for regulating the temperature of the air space trapped between hat 102 and the scalp of the wearer. Bundle 110 also includes inlet fluid line 118 and outlet fluid line 120 for passing fluid from a source of fluid 122, for example, air or water, to thermal conductive elements deployed in thermal communication with the thermoelectric elements for moderating their temperature for reasons which will become apparent hereinbelow.

Furthermore, bundle 110 preferably includes a lead 124 extending from a thermometer 126 in close vicinity to, or even actually touching, the scalp of the wearer for connection via connector 114 to thermostat apparatus 128 for controlling the temperature in the air space. Thermostat apparatus 128 preferably controls the temperature in the air space through adjustment of the electrical power supplied by power source 116, however, other modes of operation are described below.

Figure 3:
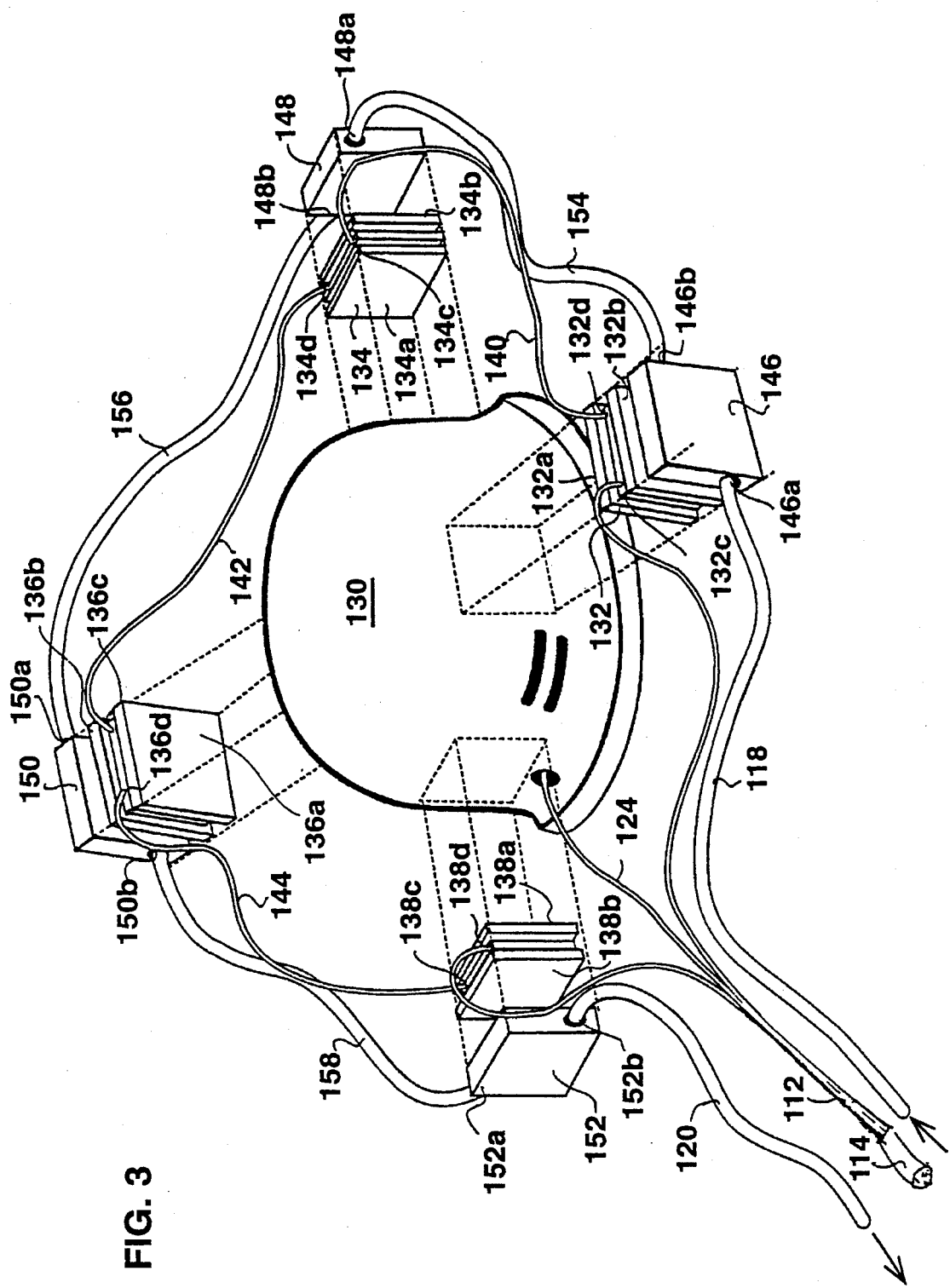
FIG. 3 shows a disassembled view of the helmet of the scalp apparatus.

Turning now to FIGS. 2 and 3, hat 102 is of a multi-ply construction including a helmet 130 having, in this case, four thermoelectric elements 132, 134, 136 and 138 for regulating the temperature of the air space trapped between helmet 130 and the scalp of the wearer. Thermoelectric elements 132, 134, 136 and 138 have surfaces 132a, 134a, 136a and 138a, respectively, disposed toward the scalp of the wearer and surfaces 132b, 134b, 136b and 138b, respectively, disposed away from the scalp of the wearer. Thermoelectric elements 132, 134, 136 and 138 can be mounted on helmet 130 according to any one of the known techniques including: adhesive bonding, compression using thermal grease or soldering. Regardless of the mounting technique employed, surfaces 132a, 134a, 136a and 138a are mounted in substantially close thermal engagement with helmet 130 such that they regulate the temperature of helmet 130. In turn, helmet 130 regulates the temperature of the air space and therefore, through natural convection, the temperature of the scalp of the wearer such that the scalp of the wearer can be maintained at a desired temperature. Typically, to maintain a scalp temperature of approximately 10° C. to effectively combat hair loss, helmet 130 is maintained at a temperature in the order of −10° C. to −20° C. It should be noted that the temperature differential between helmet 130 and the scalp of the wearer depends on how tightly fitting the wearer dons hat 102.

Helmet 130 is preferably fabricated from thermal conductive material, for example, aluminum, titanium and the like to ensure that there are no localized "cold spots" or "hot spots" in the vicinity of thermoelectric elements 132, 134, 136 and 138 and therefore the entire scalp of the wearer is substantially maintained at the same temperature. The number of thermoelectric elements depends on a number of factors including the desired temperature of the scalp of the wearer. It is a particular advantage of the present invention that through the use of natural convection to either cool or heat the scalp of a wearer rather than direct contact, the temperature of the air space can be brought to far lower and higher temperatures than with conventional apparatus to achieve improved medical benefit.

Thermoelectric elements 132, 134, 136 and 138 have positive terminals 132c, 134c, 136c and 138c, respectively, and negative terminals 132d, 134d, 136d and 138d, respectively. Thermoelectric elements 132, 134, 136 and 138 are preferably connected in series to power supply 116 for reducing the number of wires and the complexity of the wire harness of scalp apparatus 100. Depending on the manner of connection between the positive and negative terminals of power supply 116 and the terminals of thermoelectric elements 132, 134, 136 and 138, surfaces 132a, 134a, 136a and 138a, respectively, can either act as cooling surfaces for cooling the air space or heating surfaces for heating the air space depending on the type of treatment required by the wearer.

As shown, lead 112 connects to negative terminal 132c and to positive terminal 138d while a lead 140 connects positive terminal 132d to negative terminal 134c, a lead 142 connects positive terminal 134d to negative terminal 136c and a lead 144 connects positive terminal 136d to negative terminal 138c. Alternatively, thermoelectric elements 132, 134, 136 and 138 can be linked in parallel to power supply 116. In this case, thermostat apparatus 128 can control the temperature in the air space through connection and disconnection of one or more thermoelectric elements 132, 134, 136 and 138.

Elements 146, 148, 150 and 152 are mounted in substantially close thermal engagement with surfaces 132b, 134b, 136b and 138b for moderating their temperatures. Elements 146, 148, 150 and 152 are preferably fabricated from thermal conductive material, for example, aluminum and the like, and are connected to source of fluid 122 for providing a flow of fluid for passage therethrough, thereby enabling the establishment of the desired environment in the air space. In the case that helmet 102 is employed for cooling the scalp of the wearer, then source of fluid 122 provides a cool flow of fluid for cooling surfaces 132b, 134b, 136b and 138b which act as heating surfaces. In an opposite manner, in the case that helmet 102 is employed for heating the scalp of the wearer, then source of fluid 122 provides a warm flow of fluid for warming surfaces 132b, 134b, 136b and 138b which act as cooling surfaces.

Elements 146, 148, 150 and 152 are fashioned with channels (not shown) extending between inlet ports 146a, 148a, 150a and 152a and outlet ports 146b, 148b, 150b and 152b. In a similar fashion to thermoelectric elements 132, 134, 136 and 138, elements 146, 148, 150 and 152 are preferably connected in series to source of fluid 122 for providing a flow of fluid for passage therethrough. Hence, inlet line 118 is connected to inlet port 146a and outlet line 120 is connected to outlet port 152b while a tube 154 connects outlet port 146b to inlet port 148a, a lead 156 connects outlet port 148b to inlet port 150a, and a lead 158 connects outlet port 150b to inlet port 152a. Alternatively, elements 146, 148, 150 and 152 can be linked in parallel to source of fluid 122.

Hat 102 further includes inner and outer insulating layers 160 and 162 and a decorative layer 164. Insulating layer 160 preferably includes generally rectangular apemares 166 for receiving elements 146, 148, 150 and 152 and a strap 168 for coveting elements 146, 148, 150 and 152 when hat 102 is assembled. Layers 160, 162 and 164 preferably include apertures 160a, 162a and 164a for the passage therethrough of bundle 110 of wires and tubes.

Figure 4:
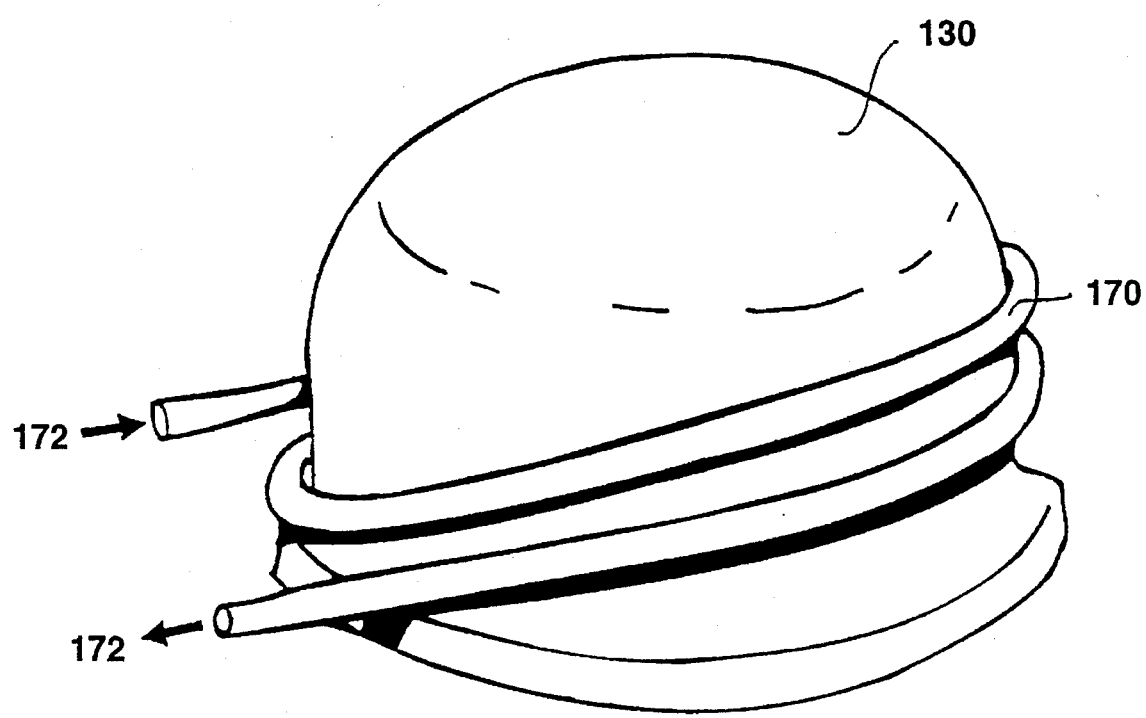
FIG. 4 shows a schematic view of a second embodiment of the helmet of the scalp apparatus.

With reference now to FIG. 4, a second embodiment of helmet 130 including a portion of piping 170 in thermal communication with helmet 130 and a source of fluid 172 for providing a flow of fluid through portion of piping 170 for regulating the temperature of helmet 130 which in turn regulates the temperature of the air space as described earlier.

The use of scalp apparatus 100 is now described for a wearer undergoing chemotherapy treatment. The wearer dons hat 102 prior to receiving a cytotoxic drug. Scalp apparatus 100 is activated for generating the cold environment surrounding the scalp of the wearer through power supply 116 providing electrical power to thermoelectric elements 132, 134, 136 and 138. At the same time, source of cooling fluid 122 passes cooling fluid through elements 146, 148, 150 and 152 to cool heating surfaces 132b, 134b, 136b and 138b. Thermoelectric elements 132, 134, 136 and 138 typically require in the order of about 10 min. to reach a temperature −10° C. to about −20° C.

When thermometer 126 registers that the temperature of the scalp of the wearer has been cooled through natural convection to approximately 10° C., thermostat control apparatus 128 is operated to maintain this temperature. At this time, the cytotoxic drug is administered to the individual in accordance with his required treatment program. Hat 102 is effective in reducing the temperature of the scalp of the wearer and the arterial blood flow around the scalp portion, thereby reducing the possibility of alopecia. The wearer continues to wear hat 102 during the drug intake and for as long after the drug intake as determined by his physician.

The use of scalp apparatus 100 has a number of advantageous features over conventional apparatus for cooling the scalp of a wearer undergoing chemotherapy by virtue of the generation of the cold air environment of typically between −10° C. to −20° C. surrounding the scalp of the wearer. First, hat 102 can be worn by virtually any adult without the need for making up special sizes because scalp apparatus 100 does not rely direct thermal contact between a thermal assembly and the scalp of the wearer. Second, the avoidance of employing cold thermal assemblies ensures that the wearer does not suffer from the uncomfortable sensation of "cold shock". Third, the wearer's hair is not wet during the operation of scalp apparatus 100 because the ambient temperature of the air in the air space is so cold that perspiration from the wearers head is immediately frozen. Fourth, the scalp apparatus 100 requires no pre-treatment in the form of hair wetting and the like before it can be donned by the user. And finally, hat 102 is particularly light such that it can be easily donned for long periods without imposing on the wearer.

While the invention has been described with respect to a limited number of embodiments, it will be appreciated that many variations, modifications and other applications of the invention may be made.

What is claimed is:

1. Scalp apparatus for regulating the temperature of the scalp of a wearer, said scalp apparatus comprising:

(a) a cap member, including:
 (i) a helmet member fabricated from thermal conductive material for covering at least a portion of the scalp of a wearer;
 (ii) thermally insulating layers for covering said helmet member;
 (iii) spacing means to provide an air space between said helmet member and the scalp of the wearer, said spacing means including a headpiece member for spacing said helmet member from the scalp of the wearer, said headpiece member having apertures for allowing direct communication of the air within said air space and the wearer's scalp; and
 (iv) a band member for embracing the hairline of the wearer, said band member connecting said thermally insulating layers, said helmet member and said headpiece member, said band member isolating the air within said air space from the surrounding atmosphere;

(b) at least one thermoelectric element connected to and in thermal communication with said helmet member for controllably heating and cooling said helmet member, including:
 (i) a first thermal surface disposed toward and in thermal communication with said helmet member and a second thermal surface disposed away from said helmet member;
 (ii) a positive and negative terminals electrically connectable to a power supply element; and (c) a power supply element for providing electrical power to said at least one thermoelectric element, said power supply element having terminals, said first thermal surface alternately functionable as a heating element and a cooling element according to the manner of electrical connection between said terminals of said at least one thermoelectric element and said terminals of said power supply element, thereby respectively heating and cooling said helmet member.

2. Apparatus as in claim 1, wherein said at least one thermoelectric element are electrically linked in series to said power supply element.

3. Apparatus as in claim 1, wherein said at least one thermoelectric element are electrically linked in parallel to said power supply element.

4. Apparatus as in claim 1, further comprising moderating means in thermal communication with said second surface of said at least one thermoelectric element for moderating the temperature of said second surface.

5. Apparatus as in claim 4, wherein said moderating means includes:

(i) at least one thermal conductive element in thermal communication with said second surface of said at least one thermoelectric element; and (ii) a source of fluid of a predetermined temperature for providing a flow of liquid through said at least one thermal conductive element for moderating the temperature of said second surface of said at least one thermoelectric element.

6. Apparatus as in claim 5, wherein said at least one thermal conductive element are linked in series to said source of fluid.

7. Apparatus as in claim 5, wherein said at least one thermal conductive element are linked in parallel to said source of fluid.

8. Apparatus as in claim 1, wherein said apparatus further includes regulating means for regulating the temperature of said helmet member so as to regulate the temperature of said air space such that the temperature of the scalp of the wearer is maintained at a desired temperature, including:

(i) a thermometer element in thermal communication with the scalp of the wearer for measuring the temperature of the wearer's scalp; and (ii) controlling means for controlling the operation of said power supply element according to the temperature sensed by said thermometer element.

9. Apparatus as in claim 1, wherein the desired temperature of the scalp of the wearer is pre-determined by the user.

10. Apparatus as in claim 1, wherein said spacing means further includes spacing members disposed between said helmet member and said headpiece member for spacing the rim of said helmet member from the rim of said headpiece member.

11. Scalp apparatus for cooling the scalp of a wearer, said scalp apparatus comprising:

(a) a cap member, including:

(i) a helmet member having relatively good thermal conductivity for covering at least a portion of the scalp of a wearer;

(ii) thermally insulating layers for covering said helmet member;

(iii) spacing means to provide an air space between said helmet member and the scalp of the wearer, said spacing means including a headpiece member for spacing said helmet member from the scalp of the wearer, said headpiece member having apertures for allowing direct communication of the air within said air space and the wearer's scalp;

(iv) a band member for embracing the hairline of the wearer, said band member connecting said thermally insulating layers, said helmet member and said headpiece member, said band member isolating the air within said air space from the surrounding atmosphere;

(b) at least one cooling element connected to and in thermal communication with said helmet member for controllably cooling said helmet member; and (c) a power supply element for providing electrical power to said at least one cooling element.

12. Apparatus as in claim 11, wherein said apparatus further includes regulating means for regulating the temperature of said helmet member so as to regulate the the temperature of said air space such that the temperature of the scalp of the wearer is maintained at a desired temperature, including:

(i) a thermometer element in thermal communication with the scalp of the wearer for measuring the temperature of the wearer's scalp; and (ii) controlling means for controlling the operation of said power supply element according to the temperature sensed by said thermometer element.

13. Apparatus as in claim 12, wherein the desired temperature of the scalp of the wearer is pre-determined by the user.

14. Apparatus as in claim 11, wherein said spacing means further includes spacing members disposed between said helmet member and said headpiece member for spacing the rim of said helmet member from the rim of said headpiece member.

15. Apparatus as in claim 11, wherein said at least one cooling element are electrically linked in series to said power supply element.

16. Apparatus as in claim 11, wherein said at least one cooling element are electrically linked in parallel to said power supply element.

* * * * *